United States Patent [19]

Frame et al.

[11] Patent Number: 5,905,028
[45] Date of Patent: May 18, 1999

[54] METHOD AND APPARATUS USEFUL FOR DETECTING BLOODGROUP ANTIGENS AND ANTIBODIES

[75] Inventors: Thomas H. Frame, Spring; David E. Hatcher; John J. Moulds, both of Houston, all of Tex.

[73] Assignee: Gamma Biologicals, Inc., Houston, Tex.

[21] Appl. No.: 08/728,751

[22] Filed: Oct. 11, 1996

Related U.S. Application Data

[63] Continuation-in-part of application No. 08/243,296, May 17, 1994, Pat. No. 5,665,558.

[51] Int. Cl.$^6$ .................. G01N 33/537; G01N 33/546; G01N 33/548; G01N 33/558
[52] U.S. Cl. .................. 435/7.25; 436/514; 436/523; 436/529; 436/533; 436/534; 436/541; 436/805; 436/824; 436/828
[58] Field of Search .................. 435/7.25; 436/514, 436/523, 529, 533, 534, 541, 805, 824, 828

[56] References Cited

U.S. PATENT DOCUMENTS

| | | |
|---|---|---|
| 3,492,396 | 1/1970 | Dalton et al. . |
| 3,905,772 | 9/1975 | Hartnett et al. . |
| 4,105,415 | 8/1978 | Lovett . |
| 4,108,972 | 8/1978 | Dreyer . |
| 4,140,662 | 2/1979 | Reckel et al. . |
| 4,244,694 | 1/1981 | Farina et al. . |
| 4,391,780 | 7/1983 | Boris . |
| 4,433,059 | 2/1984 | Chang et al. . |
| 4,435,293 | 3/1984 | Graham, Jr. . |
| 4,436,631 | 3/1984 | Graham et al. . |
| 4,472,357 | 9/1984 | Levy et al. . |
| 4,478,914 | 10/1984 | Giese . |
| 4,486,315 | 12/1984 | Teipel et al. . |
| 4,608,231 | 8/1986 | Witty et al. . |
| 4,659,658 | 4/1987 | McCarthy et al. . |
| 4,677,080 | 6/1987 | Finkelstein . |
| 4,698,311 | 10/1987 | Hall et al. . |
| 4,713,348 | 12/1987 | Ullman . |
| 4,829,011 | 5/1989 | Gibbons . |
| 4,894,347 | 1/1990 | Hillyard et al. . |
| 5,055,259 | 10/1991 | Inoue et al. . |
| 5,073,341 | 12/1991 | Hargreaves . |
| 5,086,002 | 2/1992 | Hillyard et al. . |
| 5,213,963 | 5/1993 | Uthemann . |
| 5,270,167 | 12/1993 | Francoeur . |
| 5,302,512 | 4/1994 | Pernelle . |
| 5,338,689 | 8/1994 | Yves et al. . |
| 5,460,940 | 10/1995 | Yves et al. ............... 435/33 |
| 5,512,432 | 4/1996 | Lapierre et al. ............ 435/33 |

FOREIGN PATENT DOCUMENTS

| | | |
|---|---|---|
| 2090392 | 2/1993 | Canada . |
| 0 039 195 | 11/1981 | European Pat. Off. . |
| 0 194 156 | 9/1986 | European Pat. Off. . |
| 0194 212 A1 | 9/1986 | European Pat. Off. . |
| 0 224 439 | 6/1987 | European Pat. Off. . |
| 0 305 337A1 | 3/1989 | European Pat. Off. . |
| 0363 510 A1 | 4/1990 | European Pat. Off. . |
| 0 485 228A1 | 5/1992 | European Pat. Off. . |
| 0 512 896A1 | 11/1992 | European Pat. Off. . |
| 2236181 | 3/1975 | France . |
| 2 395 780 | 3/1979 | France . |
| 2 554 240 | 5/1985 | France . |
| 8502010 | 8/1986 | France . |
| 2 660 437A1 | 10/1991 | France . |
| 2 673 472A1 | 9/1992 | France . |
| 2 035 784 | of 0000 | Germany . |
| 2 017 910 | 10/1979 | United Kingdom . |
| WO83/00296 | 2/1983 | WIPO . |
| WO 89/05456 | 6/1989 | WIPO . |
| WO 91/16116 | 10/1991 | WIPO . |
| WO 92/05442 | 4/1992 | WIPO . |
| WO 95/30904 | 11/1995 | WIPO . |
| WO95/31731 | 11/1995 | WIPO . |

OTHER PUBLICATIONS

Lapierre et al., "The gel test: a new way to detect red cell antigen–antibody reactions," Transfusion 30:109–113 (1990).

Pierce Catalog & Handbook, Life Science & Analytical Research Products, "Antibody/Protein Purification," pp. T59–T66 (1994).

Lewis et al., "Blood Group Terminology 1990," International Society of Blood Transfusion 58:152–159 (1990).

Dialog Search Report.

Wikstrom et al., "Proton Nuclear Magnetic Resonance Sequential Assignments and Secondary Structure of an Immunoglobulin Light Chain–Binding Domain of Protein L," Biochemistry 32:3381–3386 (1993).

(List continued on next page.)

*Primary Examiner*—David Saunders
*Attorney, Agent, or Firm*—Arnold White & Durkee

[57] ABSTRACT

The present invention is a method useful for the detection of bloodgroup antigens and antibodies. The method of the present invention is envisioned for two types of assays: a direct assay and an indirect assay. The direct assay comprises adding a sample of erythrocytes to a reaction tube charged with two layers of immunoreactive particles, a first layer, preferably Sepharose, having Protein G coupled to the surface of those particles and a second layer, preferably Sephacryl S-200, having Protein A coupled to those particles in a buffer solution. Antibodies specific for the bloodgroup antigens tested for are coupled to the Protein G. The reaction tube is then centrifuged for a time sufficient to force to the bottom of the reaction tube erythrocytes that do not attach to the antibodies. The indirect assay comprises obtaining samples of erythrocytes, blood serum or blood plasma to be tested and mixing the erythrocytes, serum, or plasma with a known antibody or antigen reagent, depending on whether antigens or antibodies are being tested for. The mixture is incubated in a reaction tube above two layers of immunoreactive particles, a first layer, preferably Sepharose, having Protein G coupled to the surface of those particles and a second layer, preferably Sephacryl S-200, having Protein A coupled to those particles in a buffer solution. The reaction tube is centrifuged for a time sufficient to force to the bottom of the reaction tube erythrocytes that do not attach to the Protein G.

15 Claims, 3 Drawing Sheets

OTHER PUBLICATIONS

Nilson et al., "Protein L from *Peptostreptococcus magnus* Binds to the K Light Chain Variable Domain," J. Biol. Chem. 267:2234–2238 (1992).

Kastern et al., "Protein L, a Bacterial Immunoglobulin-Binding Protein and Possible Virulence Determinant," Infect. and Immun. 58:1217–1222 (1990).

Björck et al., "Protein L from *Peptostreptococcus magnus* Binds to Affinity for Immunoglobulin Light Chains," Bacterial Immunoglobulin–Binding Proteins 1:267–278 (1990).

Kastern et al., "Structure of Peptostreptococcal Protein L and Identification of a Repeated Immunoglobulin Light Chain–Binding Domain," J. Biol. Chem. 267:12820–12825 (1992).

Nilson et al., "Purification of Antibodies Using Protein L–Binding Framework Structures in the Light Chain Variable Domain," J. Immunol. Methods 164:33–40 (1993).

Chateau et al., "On the Interaction Between Protein L and Immunoglobulins of Various Mammalian Species," Scand. J. Immunol. 37:399–405 (1993).

Patella et al., "Protein L: A Bacterial Ig–Binding Protein that Activates Human Basophils and Mast Bells," J. Immunol. 145:3054–3061 (1990).

Lämmler et al., "Characterization of Albumin–Binding Properties of *Peptostreptococcus magnus*," Can. J. Microbiol. 35:614–618 (1989).

Akerström et al., "Protein L: An Immunoglobulin Light Chain–Binding Protein Characterization of Binding and Physicochemical Properties," J. Biol. Chem. 264:19740–19746 (1989).

Björck, "Protein L: A Novel Bacterial Cell Wall Protein with Affinity for Ig L Chains," J. Immunol. 140:1194–1197 (1988).

Myhre et al., "A Non–Immune Interaction Between the Light Chain of Human Immunoglobulin and a Surface Component of a *Peptococcus magnus* Strain," Mol. Immunol. 22:879–885 (1985).

English translation of European Patent Application 594,506.

Anderson, "Analytical Techniques for Cell Fractions," Analytical Biochemistry 38:175–189 (1970).

Crowe, A.J., "Agglutination," Immunodiffusion, pp. 35–36 (1973).

Hitzler et al., "Gel Centrifugation Test—a New Micro Method for Blood Group Typing and Antibody Screening," Arztl. Lab. 35:89–92 (1989).

H. H. Fudenberg et al (EDS.) Basic & Clinical Immunology 3rd Edition, pp. 373–404 (1980).

Lisowski et al., "Sephadex Gel Filtration of Blood Cells," Archivum Immunologiae Et Therapiae Experimentals, pp. 387–390 (1966).

van Oss et al., "Influence of Various Physiochemical Factors on Hemagglutination," Vox Sang. 34:351–359 (1978).

American Association of Blood Banks Technical Manual 10th Edition, p. 279 (1990).

Lehninger, "the Molecular Basis of Cell Structure and Function," Biochemistry, pp. 141–143 (1970).

J.C. Allan et al., "The Preservation of Red Cell Antigens at Low Ionic Strength," Transfusion 30:423:426 (1990).

R. Kowal et al., "Stabilization of Proteins Immobilized on Sepharose from Leakage by Glutaraldehyde Crosslinking" Analytical Biochemistry 102:72–76 (1980).

METHOD AND APPARATUS USEFUL FOR DETECTING BLOODGROUP ANTIGENS AND ANTIBODIES

This is a continuation-in-part of U.S. patent application Ser. No. 08/243,296 now issued as U.S. Pat. No. 5,665,558, filed May 17, 1994.

FIELD OF THE INVENTION

The present invention relates generally to the field of immunoassay testing and more particularly to the detection of bloodgroup antigens and antibodies.

BACKGROUND OF THE INVENTION

The testing of blood for various antigens and antibodies has become commonplace. For example, before a patient receives a blood transfusion, a number of laboratory tests must be performed on a sample of both the patient's and the donor's blood. Specifically, the blood must be typed, to determine its ABO and Rh D bloodgroup. Before a transfusion can proceed, the patient's serum must be tested for compatibility, or cross-matched, to determine whether the serum contains antibodies to antigens present on the erythrocytes (red blood cells) of a specific donor.

Additionally, there are an increasing number of antibodies that have been determined to be present in blood serum. Determining the presence or absence of certain antibodies can have great importance, both in the diagnosis and the treatment of certain disorders.

Blood typing, compatibility testing, and antibody screening are usually done through some type of agglutination immunoassay. Agglutination assays, due to their simplicity and wide range of applications, have become one of the most common methods used in blood testing. Agglutination assays can be performed relatively simply and can be detected or read visually without resort to expensive detection equipment. In a classic simple direct agglutination assay, e.,g agglutination of group A erythrocytes by anti-A sera, cells bearing a group A antigen are agglutinated directly by antibody.

One serious drawback to this type of testing is the tendency for erythrocytes possessing weak expression of a particular bloodgroup antigen being tested for not to agglutinate or clump to an extent so that proper visual determination of the positive response is possible. Moreover, in some cases, IgG class antibodies bind to the erythrocytes with high affinity but fail to induce agglutination. Addition of anti-IgG antibodies cross links the antibodies located on the erythrocytes and causes agglutination. An example of this type of reaction is the classic indirect Coombs test in which a test serum is first incubated with test erythrocytes, the cells are washed to remove excess unbound antibodies, and then mixed with an antiglobulin serum (Coombs reagent).

Lapierre et al. reported a variation of this agglutination assay that uses inert particles in the presence of a reagent that can be either an antibody or an antigen, for typing blood components that can be either erythrocytes or serum. *Transfusion* 30:109–113 (1990). For an indirect test, the reagent (e.g., serum) and blood components (e.g., erythrocytes) are mixed and incubated for a specified period of time. The mixture is centrifuged for about 10 minutes at 70×g into a bed of inert particles (i.e., a dextran gel) in a medium containing an agglutinating reagent in solution, generally an anti-human IgG (Coombs reagent). The erythrocytes that agglutinate are trapped within the matrix of inert particles, indicating a positive reaction. In a negative reaction, the erythrocytes circumvent the particles and pellet at the bottom of the reaction tube.

Because the Lapierre method indicates a positive response by trapping the agglutinated erythrocytes on the matrix of inert particles, weak positive reactions vary significantly in appearance. Generally, in a weak positive reaction, some of the erythrocytes will pellet in the bottom of the reaction tube and others will be trapped in multiple clumps. The size of the clumps of agglutinated erythrocytes will be dependent upon the strength of the antibody/antigen reaction. Thus, where the reaction is weak, the clumps will be smaller and more likely to pass through the particle matrix. Although the Lapierre method offers an easy-to-perform test, weak positive reactions may still be difficult to read.

Accordingly, there remains room in this field for improved techniques in blood typing assays, in making an assay that is easier, more flexible and more predictable to read where there is a weak positive response. The present invention provides an improved, flexible, rapid, and accurate bloodgrouping system. The result of such a test is fewer false negative responses.

SUMMARY OF THE INVENTION

The method of the present invention is directed toward the detection of bloodgroup antigens and antibodies. The method employs immunoreactive affinity chromatography techniques to detect bloodgroup antigens and antibodies. Two types of assays are envisioned as the primary uses for the method of the present invention: a direct assay and an indirect assay.

This method uses a particle to which an antibody binding ligand is covalently bound. Thus, the particle is immunologically reactive ("immunoreactive"). The immunoreactive particle may be of various materials, although agarose is preferred. The ligand may be one of several immunoglobulin binding proteins, for example, Protein A, Protein G, Protein A/G or KappaLock, although Protein G is preferred for applications in which antibody of the IgG class is used (e.g., in a direct test) or tested for (e.g., in an indirect test).

In a particularly preferred embodiment of the present invention, immunoreactive particles are disposed in a reaction tube. The mass of immunoreactive particles in the tube creates a particle matrix. The particle matrix is comprised of two layers of particles, a first layer of particles to which an antibody binding ligand is covalently bound, preferably Protein G, and a second layer of particles to which an antibody binding ligand is covalently bound, preferably Protein A. The particles in the first layer may be of various materials, although Sepharose is preferred. The particles in the second layer of particles may be of a variety of materials, although Sephacryl is preferred. Because all of the particles are covalently bound to an antibody binding ligand, all of the particles are immunoreactive. Nonetheless, because the particles in each layer differ in the material from which the particle is made and the antibody binding ligand to which it is covalently bound, each layer of particles is a distinct layer of immunoreactive particles.

In this particularly preferred embodiment of the invention, the particles are charged to a reaction tube. The particles are disposed in the reaction tube so that the first layer of immunoreactive particles is layered above the second layer of immunoreactive particles. The preferred ratio of the first layer of immunoreactive particles to the second layer of immunoreactive particles is about 1:9.

In direct assays, erythrocytes are layered over a bed of particles in a reaction tube. The immunoreactive particles have antibody specific for the antigen of interest bound to their surface through the ligand. The reaction tube is centrifuged and non-binding erythrocytes will pellet at the bottom of the tube. A positive reaction will cause the erythrocytes to bind to the particles in the upper portion of the reaction tube and will leave a distinct line of bound red cells in the upper one-half of the reaction tube. A negative response leaves substantially all of the erythrocytes pelleted at the bottom of the reaction tube. In the case of a weak positive reaction, the erythrocytes with adequate quantity or quality of the tested for antigen will bind to the particles in the upper one-half of the reaction tube leaving a distinct zone. Most of the remainder of the erythrocytes will pellet at the bottom of the reaction tube. The binding of the erythrocytes to the particles is due to the affinity of the antigens on the red cells for the antibodies bound to the ligand on the particles.

For direct assays using a particularly preferred embodiment of the present invention, only the first layer of immunoreactive particles have antibody specific for the antigen of interest bound to their surface through the ligand. Thus, following the centrifuging of the reaction tube, non-binding erythrocytes will pellet at the bottom of the tube. A positive reaction will cause the erythrocytes to bind to the immunoreactive particles and will leave a distinct line of bound red cells in the upper portion of the immunoreactive particles in the reaction tube. A negative response leaves substantially all of the erythrocytes pelleted at the bottom of the reaction tube. In the case of a weak positive reaction, the erythrocytes with adequate quantity or quality of the tested for antigen will bind to the immunoreactive particles in the upper portion of the particles in the reaction tube leaving a distinct zone, and the remainder of the erythrocytes will pellet at the bottom of the reaction tube.

In indirect assays, erythrocytes and serum are incubated together for a sufficient time for the antigens on the surface of the erythrocytes to react with the antibodies present in the serum. The erythrocyte/serum mixture is centrifuged, exposing the erythrocyte bound antibodies to the immunoreactive particles. The centrifuging step is for a time sufficient to force any non-binding erythrocytes through the matrix of particles. A positive reaction leaves a distinct line of erythrocytes bound to the particles due to the affinity of the ligand for the antibodies that have become attached to the antigens on the erythrocytes. A negative response leaves the erythrocytes pelleted at the bottom of the reaction tube. In the case of a weak positive response, some of the erythrocytes will form a line in the upper one-half of the reaction tube and the remainder will pellet at the bottom of the reaction tube.

For indirect assays using a particularly preferred embodiment of the present invention, a positive reaction leaves a distinct line of erythrocytes bound to the immunoreactive particles in the upper portion of the particles in the reaction tube due to the affinity of the ligand for the antibodies that have become attached to the antigens on the erythrocytes. A negative response leaves the erythrocytes pelleted at the bottom of the reaction tube. In the case of a weak positive response, some of the erythrocytes will form a line in the immunoreactive particles in the upper portion of the particles in the reaction tube, and the remainder will pellet at the bottom of the reaction tube.

The reaction that binds the erythrocytes to the particles in the direct assay, i.e., an antigen/antibody reaction, is the same reaction that causes erythrocytes to agglutinate. Here, however, instead of merely forming clumps too large to pass through the spaces between the particles in the reaction tube, the cells bind directly to the particle and not to one another. Hence, the reaction of the present invention is an affinity reaction and not an agglutination reaction.

Similarly, in indirect assays, the erythrocytes become bound to the particles through the affinity that the ligand has for the antibody which has become affixed to the erythrocyte antigen during the incubation period. There is no agglutination of the erythrocytes but rather an adherence of the erythrocytes to the particles.

Thus, the method of the present invention relies upon the affinity of the erythrocytes for the particle to indicate a positive response. Consequently, positive reactions are more pronounced and definite in the method of the present invention than in those of the prior art.

DETAILED DESCRIPTION OF THE PREFERRED EMBODIMENTS

The method of the present invention is envisioned for use in two types of assays. The first is a direct assay, in which an antibody for an erythrocyte antigen is coupled to a ligand that is covalently coupled to a particle within the reaction tube. The erythrocyte is then bound to the particles through the ligand-bound antibody. The second is an indirect assay, where erythrocytes are exposed to serum antibodies and the mixture is incubated to bind the antibodies to the erythrocytes, and the erythrocyte-antibody complexes are then bound to the ligand on the particles.

The Particles

The particles used in the method of the present invention may be any particle used in agglutination assays to which a ligand may be coupled. Preferably, however, the particles are of agarose, Sepharose or latex, although other types of particles to which ligand may be coupled are also included within the scope of the invention. These particles are generally in the form of beads. Most preferred are agarose and Sepharose. These particles are in the form of beaded gels.

In a particularly preferred embodiment, the particles used in the first layer of immunoreactive particles may be any particle used in agglutination assays to which a ligand may be coupled. Preferably, however, these particles are of agarose, Sepharose or latex, although other types of particles to which ligand may be coupled are also included within the scope of the invention. These particles are generally in the form of beads. Preferred are agarose and Sepharose. Particularly preferred for use in this embodiment of the method of the present invention is Protein G Sepharose 4B Fast Flow by Pharmacia Biotech.

The particles used in the second layer of immunoreactive particles in a particularly preferred embodiment of the method of the present invention should meet the following criteria:

(1) When mixed with preferred Protein G Sepharose 4B Fast Flow particles, the non-Sepharose particle should sediment in the reaction container in such a way that the Sepharose particles form a layer on top of the particles, i.e., the non-Sepharose particles settle faster than the Sepharose particles; and (2) The non-Sepharose particles when mixed with the Protein G Sepharose 4B Fast Flow particles must be fluid enough to enable satisfactory filling of a reaction tube array.

Particularly preferred particles for use in the second layer of immunoreactive particles are Sephacryl S-100, S-200 and S-400. Most preferred is Sephacryl S-200.

Figure 1A:
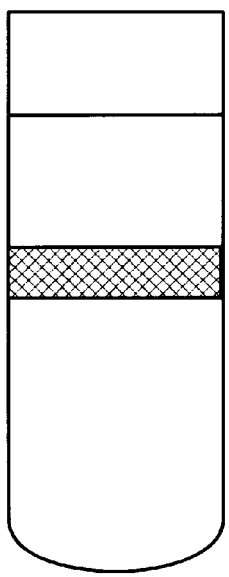
FIG. 1A is a side view of a strong positive reaction wherein the binding erythrocytes form a very distinct and broad line in the upper one-half of the reaction tube.
Figure 1B:
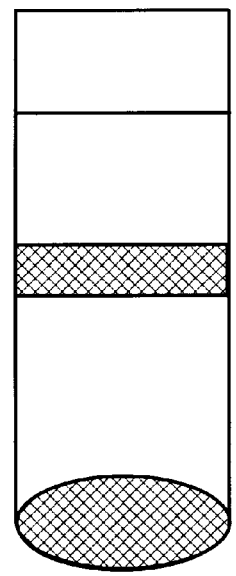
FIG. 1B is a side view of a weak positive reaction wherein an adequate quantity or quality of antigen/antibody reaction causes the erythrocytes to bind to the particles forming a distinct line in the upper one-half of the reaction tube. The erythrocytes not creating the quantity or quality of antigen/antibody reaction to cause the same binding will be forced to pellet in the bottom of the reaction tube.
Figure 1C:
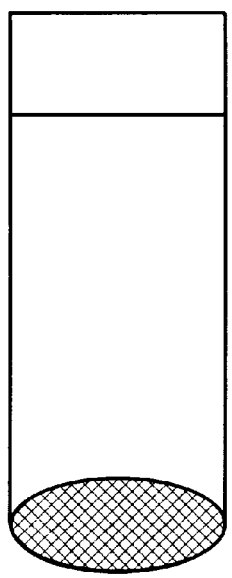
FIG. 1C is a side view of a negative reaction wherein none of the erythrocytes create the antigen/antibody reaction necessary to bind the erythrocytes to the particles and as they did not bind to the particles are forced to pellet in the bottom of the reaction tube.
Figure 1D:
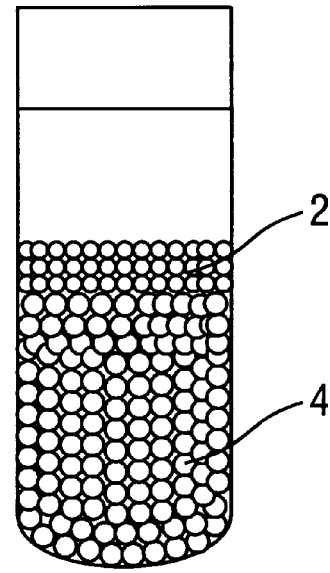
FIG. 1D is a side view of a reaction tube filled with the first and second layers of immunoreactive particles matrix of a particularly preferred embodiment of the present invention.

As depicted in FIG. 1D, the second layer of immunoreactive particles 4 occupy the greatest volume of the reaction tube and the first layer of immunoreactive particles 2 is disposed above the second layer of immunoreactive particles.

The Ligands

A number of ligands are known that bind immunoglobulin molecules and may be covalently coupled to the particles, for example Protein A, Protein G, Protein A/G and KappaLock. Protein G is a particularly preferred ligand for use in assays where IgG immunoglobulins are used or tested for. One reason that Protein G is preferred is that it has a greater affinity than Protein A for most IgG immunoglobulins. Protein G also binds with a significantly greater affinity than Protein A to certain subclasses of IgG, e.g., human IgG3, mouse IgG1 and rat IgG2a. Protein G does not bind to human IgM, IgA and IgD.

Protein G is a bacterial cell wall protein isolated and purified from group G streptococci. Protein G binds to mammalian IgG immunoglobulins through their Fc portion. Because Protein G only binds the Fe portion of IgG immunoglobulins, the antibody portion of the immunoglobulin remains available for reaction with its corresponding antigen, yet the immunoglobulin remains bound to the particle. Native Protein G has been sequenced by DNA analysis. From the DNA analysis, two IgG binding domains and sites for albumin and cell surface binding have been identified.

ImmunoPure® Immobilized Protein G is a commercially available particle product having Protein G immobilized on the surface of agarose gel bead particles. This product is available from Pierce of Rockford, Ill. The immobilized Protein G has been genetically engineered to remove the albumin and cell surface binding regions and thereby minimize the binding of anything other than immunoglobulins.

ImmunoPure® Immobilized Protein G consists of a recombinant Protein G covalently linked (glutaraldehyde activation of the beads) to cross-linked 6% beaded agarose. The material is supplied in a 50% slurry. The material can bind 11 mg of human IgG per ml of gel.

Protein A is a cell wall component produced by several strains of Staphylococcus aureus. Protein A is capable of specifically binding the Fc region of immunoglobulin molecules, especially IgG. The Protein A molecule has four high affinity binding sites that are capable of interacting with the Fc region from IgG of several species. Protein A interacts with some IgG subgroups and not with others. For example, human IgG1, IgG2 and IgG4 bind strongly while IgG3 does not bind. And, there are also some instances in which monoclonal antibodies do not bind to Protein A.

Immobilized Protein A is also available commercially from Pierce. This immobilized Protein A is a highly purified Protein A, covalently coupled to cross-linked beaded agarose. The typical binding capacity for this immobilized Protein A is 12–15 mg of human IgG per milliliter of gel.

Protein A/G is a genetically engineered protein that combines the IgG binding profiles of both Protein A and Protein G. Protein A/G is a gene fusion product secreted from a non-pathogenic form of Bacillus. This genetically engineered Protein A/G is designed to contain four Fc binding domains from Protein A and two from Protein G.

Protein A/G binds to all human IgG subclasses. In addition, it binds to IgA, IgE, IgM and to IgD but to a lesser extent to IgD. Thus, Protein A/G may be a preferred ligand in tests for or tests using non-IgG class immunoglobulins.

Pierce also offers an immobilized Protein A/G covalently coupled to beaded agarose under the trade name ImmunoPure® Immobilized Protein A/G.

KappaLock is a universal kappa light chain binding protein available from Aaston, Inc., 12 Falmouth Road, Wellesley, Mass. It has been genetically engineered from the DNA of a strain of Peptostreptococcus. This protein binds to the kappa region of the light chain of all antibody types. KappaLock has been genetically engineered to delete the albumin and cell wall binding regions of the naturally occurring bacterial protein. The resultant engineered protein has four antibody binding domains and specifically does not bind to heavy chains or to the Fc region of immunoglobulins. Because kappa light chains are shared among different classes of antibodies, KappaLock will bind to antibodies having a kappa light chains regardless of heavy chain class.

KappaLock may be immobilized on various supports, particularly on agarose beads. Immobilized KappaLock will capture mouse IgG, rabbit IgG, human IgG, human IgA and human IgM.

All of the preferred ligands may be covalently bound to a solid-phase matrix such as agarose beads (e.g., Sepharose Pharmacia) using known techniques, for example as described by Hearn et al., Methods in Enzymology Vol. 35:102–117 (1987). Generally, the beads are first activated by a chemical agent, such as glutaraldehyde, carbonyldiimidizole, cyanogen bromide hydroxysuccinimide, tosyl chloride or the like. The chosen ligand is then covalently attached to the beads, resulting in an extremely stable linkage of the ligand to the support.

In a particularly preferred embodiment, the ligand used in the first layer of immunoreactive particles may be one of several immunoglobulin binding proteins, for example, Protein A, Protein G, Protein A/G or KappaLock™, although Protein G is preferred for applications in which antibody of the IgG class is used (e.g., in a direct test) or tested for (e.g., in an indirect test). Protein A is particularly preferred for the second layer of immunoreactive particles.

The particularly preferred particles for use in the second layer of immunoreactive particles may be obtained without a ligand bound to the particles. In that event, the procedure set out below in Steps A and B is preferred:

A. Glutaraldehyde Activation of Sephacryl S-200

1. Wash the required amount of saline-washed Sephacryl S-200 three with 0.5M sodium phosphate buffer, pH 7.5.
2. In a fume hood, add equal volumes of 6.25% glutaraldehyde in 0.5M sodium phosphate buffer, pH 7.5.
3. Measure the pH of the mixture and adjust as necessary. This should be in the range of 7.2–7.6.
4. Incubate the mixture overnight at 37° with gentle mixing on a rotator.
5. Wash the activated Sephacryl S-200 two times with 0.5M sodium phosphate buffer, pH 7.5. The Sephacryl S-200 is now ready for coupling.

B. Protein A coupling to activate Sephacryl S-200

1. Add an equal volume of a solution containing from about 100 µg/ml–5000 µg/ml, with about 250 µg/ml being preferred of recombinant Protein A (Pierce) in 0.5M sodium phosphate buffer, pH 7.5. Incubate overnight at room temperature on a rotator.
2. Wash the activated Protein A Sephacryl gel two times with 0.5M sodium phosphate buffer, pH 7.5 and one time with a solution containing 1M NaCl in 0.05M sodium phosphate buffer, pH 7.5.
3. Add an equal volume of 0.5M ethanolamine in 0.5M sodium buffer pH 7.5. Incubate for four hours at room temperature on a rotator.
4. Wash the activated Protein A Sephacryl three times with 0.9% NaCl and two times with ReACT gel buffer.
5. Resuspend the activated Protein A Sephacryl with 1.5 volumes of ReACT gel buffer Those skilled in the art will recognize that other methods may be used to bind the ligand to the inert particles.

Through experience, it has been learned that the ligands, particularly Protein G, may leach off prepared immunoreactive particles such as Protein G Sepharose 4B Fast Flow. Such leaching is undesirable because it reduces the effective shelf life of prepared particles and may lead to incorrect test results. Treatment of prepared immunoreactive particles with glutaraldehyde has been shown to increase the binding effectiveness of the ligand to the particle.

A preferred glutaraldehyde treatment is described in R. Kowal, R. G. Parsons, *Analytical Biochemistry*, Vol. 102: 72–76 (1980). That treatment comprises adding 4 volumes of about 0.015% (v/v) glutaraldehyde (Sigma Chemical Company) in a sodium carbonate buffer (pH about 8.8) to prepared immunoreactive particles and let the mixture stand for one hour. After one hour, the supernate is aspirated and about 1M Tris-HCl (pH about 7.8) added to block any untreated aldehyde groups. The mixture is incubated for about one hour at room temperature. After one hour, the Tris buffer is aspirated and the particles washed with 1.2% NaCl containing 7.5% (w/v) Ficoll 400, 5% (v/v) BSA (Buffer 1) four times using the following steps: (1) Add buffer 1, (2) let the particles sediment, (3) aspirate buffer 1, and (4) repeat.

Antibodies and Antigens

The antibody or antigen used as a reagent is dependent upon the antibody or antigen that is being tested for. The number of blood antigens and thus, antibodies that have been identified is very large, with more antigens and antibodies continually being determined. The International Society of Blood Transfusion has published an article titled *Bloodgroup Terminology* 1990, Vox. Sang. 58:152–169 (1990), which is expressly incorporated herein by reference. A non-exclusive list of red cell antigens for which the present method would be suitable is found on page 153. However, the following antibodies and antigens are particularly preferred: A, B, D, C, c, $C^w$, E, e, K, $Fy^a$, $Fy^b$, $Jk^a$, $Jk^b$, S and s.

In adapting the method for use in testing for the various antibodies and antigens of interest, one should select a ligand capable of binding to the isotype of the antibody that is used or tested for or, alternatively, one may use a bridging antibody, e.g., an IgG anti-IgM, for an IgM antibody. Thus, an IgG anti-IgM antibody would be coupled to the ligand as a "bridge" and an IgM antibody would bind to the IgG anti-IgM antibody.

The Direct Assay

For direct assay, the immunoreactive particles may be prepared as follows: the particles with covalently coupled ligand are first centrifuged and the supernate is removed and discarded. An appropriate amount of properly diluted antibody reagent is gently mixed with the particles, and the mixture is allowed to stand for about 15 minutes so as to allow the antibody to bind to the ligand on the particles. The amount of diluted antibody reagent added to the particles will depend upon the source and concentration of the antibody to be used. The mixture is centrifuged, and the supernate is removed and replaced by a non-antibody containing solution, for example a buffered solution containing dextran. Thus, the immunoreactive particle suspension will generally contain little or no free antibody in solution.

A particularly preferred buffer solution contains Ficoll 400, BSA, $NaN_3$ and NaCl (ReACT gel buffer available from Gamma Biologicals, Inc.). In 1000 ml of ReACT gel buffer is the following:

| Ingredient | Amount | Final Conc. |
|---|---|---|
| 50% Ficoll 400 (Pharmacia) | 150 ml | 7.5% |
| 30% BSA (salt free) | 166 ml | 5.0% |
| 25% $NaN_3$ | 4.0 ml | 0.1% |
| NaCl 12 g/L | 680 ml | n.a. |

After mixing the above ingredients, the solution should be filtered and the pH should be measured. The pH should be about 7.2 at 20° C.

An appropriate amount of the immunoreactive particle suspension, e.g., 20–150 µl, is pipetted into the reaction tube, and the particles are allowed to settle to the bottom of the tube, resulting in a substantially particle free zone of dextran-buffer covering the particles. In some embodiments, a number of neutral particles, i.e., those not having ligand bound to the surface of the particles, may be mixed with the immunoreactive particles in order to make the assay less expensive to perform.

In a particularly preferred embodiment, appropriate amounts of each type of immunoreactive particles are washed three times with 0.9% NaCl and then three times with a solution consisting of 1.2% NaCl containing 7.5% (w/v) Ficoll 400 and 5% (v/v) BSA (Buffer 1). After the last wash, the supernate is removed completely from each sample and each particle samples is resuspended in 1.5 volumes of fresh Buffer 1 with thorough mixing. The particle samples are then combined in the ratio of about 1 part of first layer inmmunoreactive particles to about 9 parts second layer immunoreactive particles. One of ordinary skill in the art will understand that other preparatory steps may be used and other ratios of particles may be equally effective.

An appropriate amount of the first and second layer immunoreactive particle mixture, e.g., 20–150 µl, is pipetted into the reaction tube, and the particles are allowed to settle to the bottom of the tube. Alternatively, the reaction tube may be centrifuged for about 15 seconds at about 1000 g. In either event, what results is a substantially particle free zone of buffer covering the particles.

Preparation of the Erythrocytes

Generally, the erythrocytes to be tested will have been drawn from a patient and submitted for determination of the presence of certain bloodgroup antigens. The erythrocytes are separated from the whole blood by traditional techniques, and a suspension of erythrocytes in the range of about 0.5–1.0% (w/v) is prepared in a low ionic strength solution. Gamma N-HANCE® by Gamma Biologicals, Inc., may be used for this solution. A low ionic strength solution adapted from J. C. Allan, et al., *Transfusion*, Vol. 30: 423–26 (1990) is particularly preferred for this purpose.

An appropriate amount of a suspension of erythrocytes, e.g., 15–75 µl of a 0.5–1% suspension, is added to the reaction tube and the reaction tube is centrifuged for a time sufficient to force the non-binding erythrocytes to the bottom. Preferably, the centrifuge has a rotor adapted so that the centrifugal force generated by the centrifuge acts along the long axis of the reaction tube. Consequently, the centrifugal force generated during the centrifuging step will operate to more forcefully urge the non-binding erythrocytes to pellet in the bottom of the reaction tube.

The Centrifugation Step

Those of ordinary skill in the art will recognize that the centrifugation conditions used will depend on a number of factors, e.g., the design and type of the reaction vessel used and the centrifuge used. A two- or three-step centrifugation procedure is preferred. Generally, the initial centrifugation step is for a short period of time ranging from about 10–30 seconds at a high centrifugal force ranging from about 800–1200 g in order to force the erythrocytes through the dextran solution. A second centrifugation step is used to bring the erythrocytes into contact with the immunoreactive particles. This step can be performed at a lower centrifugal force, ranging from about 300–600 g for about 15–45 seconds. A third centrifugation step is used to force the unbound erythrocytes through the bead matrix. The third centrifugation may be performed at a high centrifugal force ranging from about 800–1200 g or the more preferred range of about 1300–1600 g for a period of about 45–90 seconds. The third centrifugation step considerably reduces the time needed to perform the separation of binding and non-binding erythrocytes. Separation is also possible by extending the duration of the second centrifugation step for about 5–10 minutes.

The Indirect Assay

In the indirect assay, an appropriate amount of immunoreactive particles, e.g., 15–150 µl having the ligand bound to the surface of the particles is obtained and an appropriate amount of a diluent, such as buffered saline containing dextran, e.g., 30–300 µl, is mixed with the particles. When performing an indirect assay for an antibody screening, it may be advantageous to use a dextran/saline buffer having a pH of about 7. An appropriate amount of the mixture, e.g., 20–150 µl, is pipetted into a reaction tube and the particles are allowed to settle for approximately 15 minutes, resulting in a substantially particle free zone of dextran-buffer covering the particles.

An appropriate amount of potentiator, e.g., 15–100 µl, is added to the reaction tube. An appropriate amount of a suspension of erythrocytes, e.g., 15–75 µl, is suspended in a suitable medium, such as a low ionic strength potentiator solution. The potentiator acts to enhance and increase the speed at which the antigen or antibody binding occurs and creates a more profound positive reaction if one is to occur. A particularly preferred potentiator is a low ionic strength enhancement solution sold under the trade name Gamma N-HANCE® marketed by Gamma Biologicals, Inc., Houston, Tex. An appropriate amount of a suspension of erythrocytes to be tested, e.g., 15–75 µl of a 0.5–1% suspension, is suspended in the potentiator solution, followed by the addition of an appropriate amount of test serum, e.g., 15–75 µl. The reaction tube is then incubated under conditions sufficient for the antibody/antigen reaction to occur. Preferred conditions are incubation for approximately 5–30 minutes at about 37° C., and more preferred is an incubation time of about 10 minutes.

The reaction tube is then centrifuged for a time sufficient to force non-binding erythrocytes through the spaces between the particles, forcing them to pellet at the bottom of the reaction tube.

Using a particularly preferred embodiment in the indirect assay, appropriate amounts of first and second layer immunoreactive particles are washed three times with 0.9% NaCl and then three times with a solution consisting of 1.2% NaCl containing 7.5% (w/v) Ficoll 400 and 5% (v/v) BSA (Buffer 1). After the last wash, the supernate is removed completely from each sample and both particle samples are resuspended in 1.5 volumes of fresh Buffer 1 with thorough mixing. The particle samples are then combined in the ratio of about 1 part of first layer immunoreactive particles to about 9 parts second layer immunoreactive particles. One of ordinary skill in the art will understand that other preparatory steps may be used and other ratios of particles may be equally effective.

An appropriate amount of the mixture, e.g., 20–150 µl, is pipetted into a reaction tube and the particles are allowed to settle for approximately 15 minutes, resulting in a substantially particle free zone of buffer covering the particles. Alternatively, the reaction tube may be centrifuged for about 15 seconds at about 1000 g to achieve the same result.

An appropriate amount of test serum or plasma, e.g. 15–75 µl, is added to the reaction tube. An appropriate amount, e.g. from 15–75 µl, of erythrocytes suspended in preferably the low ionic preservation solution adapted from the Allan article in *Transfusion* is then added to the reaction tube. The preferred concentration for the erythrocyte suspension is about 0.8%. The reaction tube is then incubated under conditions sufficient for the antibody/antigen reaction to occur. Preferred conditions are incubation for approximately 5–30 minutes at about 37° C., and more preferred is an incubation time of about 15 minutes.

The reaction tube is then centrifuged for a time sufficient to force non-binding erythrocytes through the particle matrix, forcing them to pellet at the bottom of the reaction tube.

In comparing the indirect assay with the direct assay, it will be noted that in the indirect assay, the antibodies are added to the erythrocytes and that mixture incubated prior to the centrifuging step. Thus, the antibodies and antigens have the opportunity to react before the erythrocytes are exposed to the particles and the attached ligand. In the direct assay, the antibodies are coupled to the ligand on the particles and the erythrocytes are not exposed to the antibodies until the erythrocytes are forced through the spaces between particles by the centrifuge.

In the indirect assay, the erythrocytes that react with antibodies in the test serum bind to the particles through the interaction between the antibodies that attach to the antigens on the erythrocytes and the ligand on the particle. The detection of a positive reaction is the same as in the direct assay, in that a positive response results in a strong line of bound erythrocytes in the upper one-half of the reaction tube, a weak positive response results in a line of bound erythrocytes in the upper one-half of the reaction tube and generally some non-binding erythrocytes pelleted at the bottom of the tube, and a negative response results in all the non-binding erythrocytes pelleted at the bottom of the reaction tube.

The reaction tube used in the method of the present invention is not critical. The most important factor to consider is that the tube provide an adequate column height of particles so that the affinity reaction can occur during centrifugation.

Microwells in microliter plates have been used successfully wherein a 3 to 4 mm column of particles is present. Also useful are microfuge tubes and the like.

Figure 2A:
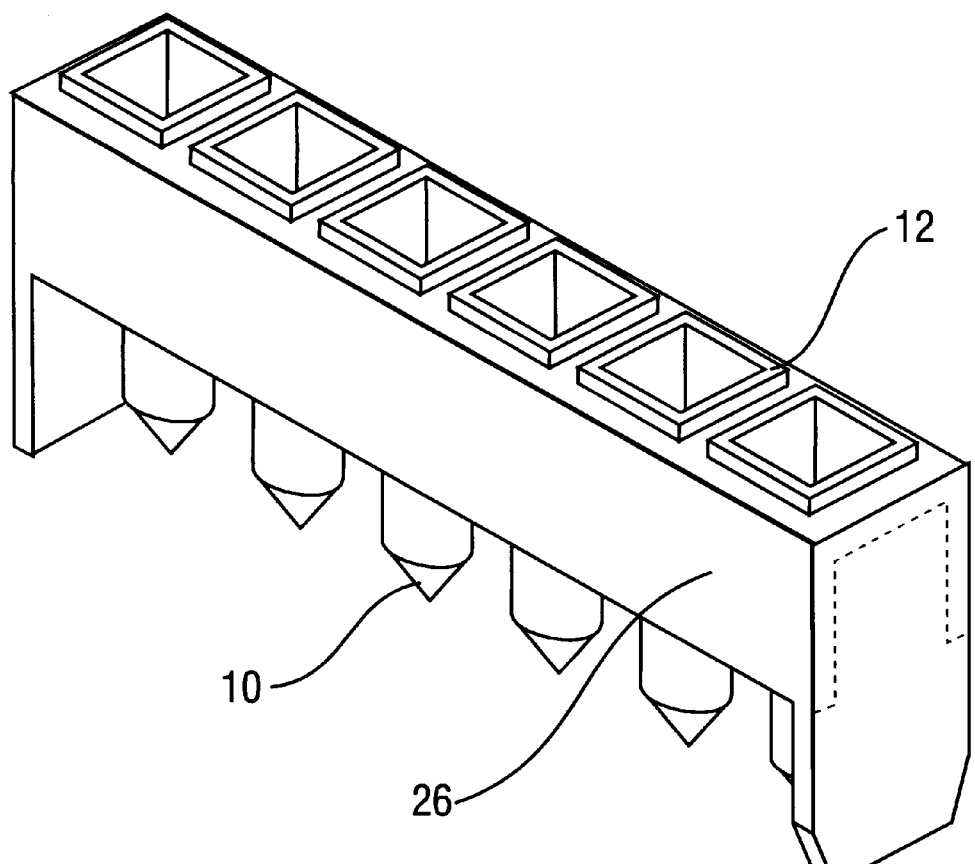
FIG. 2A is a perspective view of a preferred single unit 6-tube array.

In a preferred embodiment, a plurality of reaction tubes can be joined to produce a single unit tube array, for example, as shown in FIG. 2A. FIG. 2A shows a single unit tube array comprising six reaction tubes 10. Each reaction tube is sealable at its top 12 so that the array may be sold prefilled with activated particles suitable for use in direct assays, indirect assays or a mixture thereof.

Figure 2B:
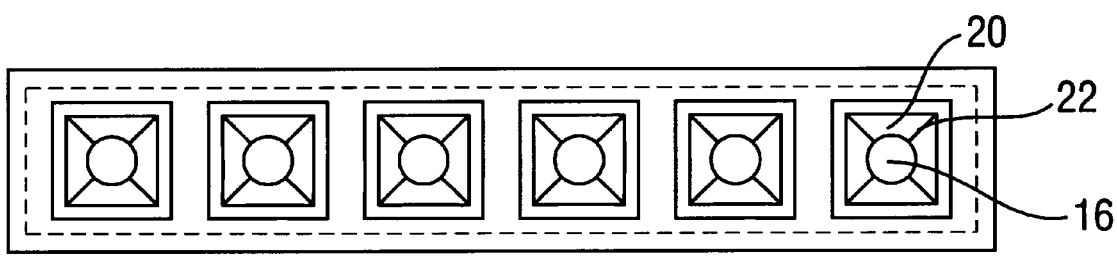
FIG. 2B is a top view of the same single unit 6-tube array.
Figure 2C:
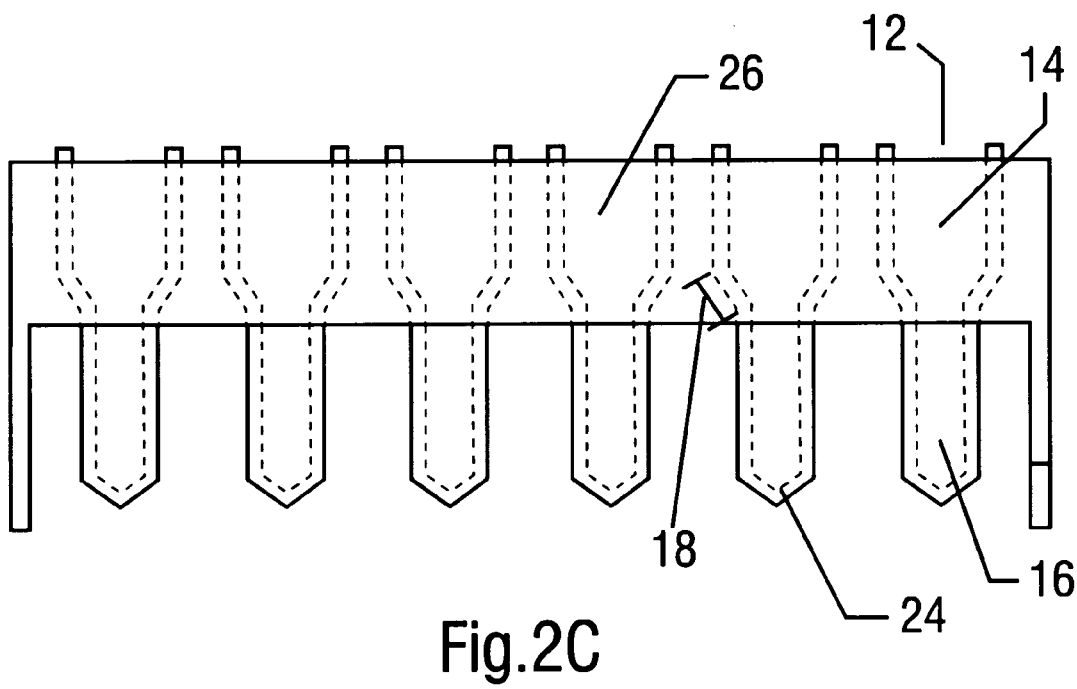
FIG. 2C is a side view of the same single unit 6-tube array.

As seen in FIG. 2C, each reaction tube is substantially wider at the top, forming a reaction well 14 above the tube portion 16 of the reaction tube. The reaction well narrows in a tapering zone 18 so that during the centrifugation step, the erythrocytes present in the reaction well are directed into the tube portion of the reaction tube. When prefilled, the reaction tubes will be filled with immunoreactive particles and dextran solution into the tapering zone.

FIG. 2B shows that the tapering zone possesses four planar surfaces 20 with valleys 22 at the intersection of each of the planar surfaces. Each planar surface is broadest at the top of the zone where it meets the reaction well and then each surface gradually narrows through the zone until it reaches the reaction tube at the termination of the tapering zone.

Each reaction tube has a pointed terminus 24. This configuration causes non-binding erythrocytes to collect in the pointed terminus of the reaction tube in a pronounced pellet. The tube portion 16 of the reaction tube is to be dimensioned to provide a column of immunoreactive particles about 3–4 mm in height. The array is designed to have a labelling surface 26 for affixing identifying information.

Figure 2D:
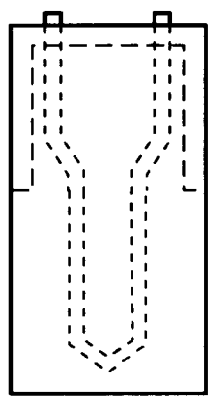
FIG. 2D is an end view of the same single unit 6-tube array showing a squared-off base.
Figure 2E:
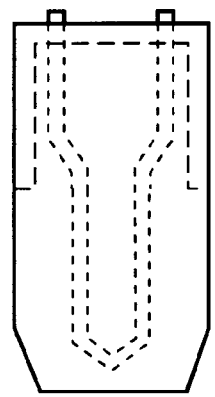
FIG. 2E is an end view of the end opposite that shown in FIG. 2D and showing a slightly narrower base than seen in FIG. 2D.

As seen in FIGS. 2D and 2E, each end of the single unit tube array is different, creating an index for orientation of these arrays during mass filling of the reaction tubes. Thus, one end of the array may be distinguished from the other.

The unit tube array may be manufactured using any suitable material, such as plastics and the like, but preferably is made of TPX®, a biologically and chemically inert plastic generically known as polymethylpentene. TPX® is supplied by Mitsui Petrochemicals (America) Ltd.

In one embodiment, e.g., for a direct test, the tubes in the array may be custom filled with a preselected variety of antibodies bound to the ligand. For example, a preferred array for blood typing may contain the following antibodies: anti-A, anti-B, anti-AB, anti-D (e.g., F8D8), anti-D (e.g., GAMA-401) and a suitable control (ligand only).

The following examples are provided so as to enable those of ordinary skill in the art to practice the method of the invention. These examples are not intended to limit the scope of what the inventors regards as their invention. Efforts have been made to ensure accuracy with respect to numbers used to characterize the measured conditions; however, some experimental errors and deviations may be present.

EXAMPLE 1

Testing for the Presence or Absence of the A Bloodgroup Antigen on Erythrocytes using a Direct Assay A. Preparation of Specific Anti-A Agarose Beads Two ml of ImmunoPure® Immobilized Protein G were centrifuged for about two minutes at 1000 g and the supernate removed and discarded. Two ml of a pre-diluted sample of a mouse monoclonal anti-A (clone 46G5 mouse IgG3 isotype) were added. The monoclonal anti-A was diluted in 0.01M citrate buffered saline (pH 5.0) containing 7.5% Dextran (w/v). The contents were mixed gently and allowed to stand for 15 minutes. The agarose/antibody mixture was centrifuged for approximately two minutes at 1000 g and the supernate removed and tested for residual anti-A activity in an agglutination assay.

That testing was performed in the following manner: a sample of the supernate was tested for its ability to agglutinate A positive erythrocytes. No agglutination was observed, indicating complete binding of the antibodies to the particles.

B. Preparation of the Reaction Tubes

Individual microwells of a microliters plate (Thermowell polycarbonate microtiter plate Costar) were used as reaction tubes. The specific anti-A agarose beads were thoroughly mixed and 70 μl of the mixture was pipetted into each microwell. The agarose beads were allowed to settle to the bottom of the well before further testing (approximately 15 minutes).

C. Test Procedure

Erythrocytes were obtained from either citrated blood samples or liquid nitrogen storage. The blood samples had been previously typed using FDA approved anti-A and anti-AB bloodgrouping reagents. A 0.8% suspension of the sample erythrocytes was prepared using a low ionic strength solution (Gamma N-hance, Gamma Biologicals, Inc.). Fifteen microliters 15 μl of the approximate 0.8% suspension of erythrocytes were pipetted into each microwell. The microwells were then centrifuged for 15 seconds at 900–1000 g, 30 seconds at 500 g, and finally for 45 seconds at 900–1000 g in a Serofuge II (Clay-Adams), using a modified rotor so that the centrifugal force acts along the long axis of the reaction tube.

D. Results/Interpretation

If the erythrocytes possess the A bloodgroup antigen, they will adhere to the anti-A agarose beads at the top of the matrix (FIG. 1A). If the erythrocytes possess a weak expression of the A bloodgroup antigen, e.g., $A_3$ or $A_x$, then some erythrocytes will adhere to the anti-A agarose beads at the top of the matrix and some will collect at the bottom of the wells (FIG. 1B). If the erythrocytes do not possess the A antigen, all the erythrocytes will collect at the bottom of the wells (FIG. 1C). The results observed in this experiment are shown below in Table 1.

TABLE 1

| | ABO BLOODGROUP | | | | | | | |
|---|---|---|---|---|---|---|---|---|
| | $A_1$ | $A_2$ | $A_1B$ | $A_2B$ | $A_3$ | $A_z$ | B | O |
| No. Tested | 10 | 8 | 6 | 2 | 2 | 2 | 10 | 10 |
| No. Positive | 10 | 8 | 6 | 2 | 2 | 2 | 0 | 0 |

Testing erythrocytes for the presence or absence of the B bloodgroup antigen can be performed in a similar manner by substituting an anti-B for the anti-A reagent.

The source of the antibody can be either human polyclonal, human monoclonal or mouse monoclonal, etc. If the immunoglobulin class of the antibody is not IgG, then the antibody can be attached to a Protein G ligand by means of a second antibody, e.g., anti-human IgM or anti-kappa or anti-lambda, provided that this secondary antibody is of the IgG class. Alternatively, if Protein A/G is bound to the gel particles, any antibody class to which Protein A/G binds may be used.

EXAMPLE 2

Testing for the Presence or Absence of the Rh D Antigen or Erythrocytes by Direct Assay The erythrocytes were obtained from either citrated blood samples or liquid nitrogen storage. The erythrocytes had been previously typed using FDA approved anti-D blood-grouping reagents. A 0.8% suspension of the erythrocytes was prepared in a low ionic strength solution (Gamma N-HANCE®, Gamma Biologicals, Inc.).

The preparation of the reaction tubes and test procedure are identical to those previously described in Example I except that an IgG1 anti-D (human monoclonal clone F8D8) was substituted for the anti-A antibodies.

A. Results/Interpretations

If the erythrocytes possess a normal expression of the rhesus D antigen, they will adhere to the anti-D agarose particles at the top of the solid phase matrix (FIG. 1A). If the erythrocytes possess a weak (quantitative) expression of the D antigen, e.g., $D^u$, or a qualitative variant of the D antigen, e.g., DVI variant, then some of the erythrocytes will adhere to the anti-D agarose particles at the top of the matrix and some will collect at the bottom of the wells (FIG. 1B). If the erythrocytes do not possess the rhesus D antigen, all the erythrocytes will collect at the bottom of the wells (FIG. 1C). The results observed in this experiment are shown below in Table 2.

TABLE 2

|  | Rh D | | | |
| --- | --- | --- | --- | --- |
|  | Rh D Positive | Rh D Negative | DVI Variant | Weak D ($D^u$) |
| No. Tested | 10 | 6 | 3 | 3 |
| No. Positive | 10 | 0 | 3 | 2 |

Testing erythrocytes for the presence or absence of other Rh antigens, e.g., C, c, E or e, etc. can be performed in a similar manner by substituting that specific reagent for the anti-D antibodies. The source of the antibodies can be either human polyclonal (e.g., affinity purified), human monoclonal or mouse monoclonal, etc. If the immunoglobulin class of the antibody is not IgG, then the antibody can be attached to a Protein G ligand by means of a second antibody, e.g., anti-human IgM or anti-kappa or anti-lambda, provided that this secondary antibody is of the IgG class. Alternatively, if Protein A/G is bound to the gel particles, any antibody class to which Protein A/G binds may be used.

EXAMPLE 3

Testing for the Presence or Absence of the $Fy^a$ Antigen on Erythrocytes by Indirect Assay This test procedure was performed with non-affinity purified human polyclonal antisera.

A. Preparation of Protein G Agarose Particles

Two ml of immobilized Protein G (ImmunoPure® G) were centrifuged for about two minutes at 900–1000 g and the supernate removed and discarded. Two ml of a 0.01M citrate buffered saline (pH 5.0) solution containing 7.5% Dextran (w/v) were added to the Protein G and mixed thoroughly.

B. Preparation of the Reaction Tubes

Seventy microliters 70 µl of the Protein G mixture from above were pipetted into microwells in a microtiter plate (Thermowell polycarbonate microtiter plate Costar). The agarose particles were allowed to settle to the base of the wells (approximately 15 minutes).

C. Test Procedure

Fifty microliters 50 µl of a low ionic strength enhancement solution (Gamma N-HANCE®, Gamma Biologicals, Inc.) were added to each well. The erythrocytes were obtained either from citrated blood samples or from commercially available reagent erythrocyte panels (Gamma Biologicals, Inc.) and had been previously typed using FDA approved anti-$Fy^a$ bloodgrouping reagent. A 0.8% suspension of the erythrocytes was prepared using a low ionic strength solution. Fifteen microliters 15 µl of the 0.8% suspension of the erythrocytes to be tested were added to each well followed by 25 µl of an anti-$Fy^a$ reagent test serum. The microwells were then incubated for 10 minutes at 37° C.

The microwells were then centrifuged for 15 seconds at 900–1000 g, 30 seconds at 500 g, and 45 seconds at 900–1000 g in a Sero-fuge II (Clay-Adams) using a modified rotor so that the centrifugal force acts directly along the axis of the reaction tube.

D. Results/Interpretation

If the erythrocytes possess the $Fy^a$ bloodgroup antigen, they will adhere to the Protein G agarose particles at the top of the matrix (FIG. 1A). If the erythrocytes do not possess the $Fy^a$ bloodgroup antigen, they will collect at the bottom of the wells (FIG. 1C). The results observed on this experiment are shown below in Table 3.

TABLE 3

| $Fy^a$ Antigen Typing Duffy Bloodgroup Phenotype | | | |
| --- | --- | --- | --- |
|  | Fy(a+b−) | Fy(a+b+) | Fy(a−b+) |
| No. Tested | 10 | 10 | 8 |
| No. Positive | 10 | 10 | 0 |

This test procedure could be used to type erythrocytes for any erythrocyte antigen in combination with a polyclonal or monoclonal antiserum containing specific IgG antibodies to the erythrocyte antigen.

EXAMPLE 4

Antibody Screening or Compatibility Testing by Indirect Assay

The erythrocytes used were from commercially available reagent erythrocyte panels (Gamma Biologicals, Inc.) that had been previously typed for specific antigens using FDA approved bloodgrouping reagents, where available, by the manufacturer. The sera samples were obtained from patient samples referred to the consultation laboratory of Gamma Biologicals, Inc. Each serum sample was tested with at least one erythrocyte suspension expressing the antigen against which the antibody was directed (positive control), and with at least one erythrocyte suspension lacking the antigen recognized by the antibody (negative control).

The preparation of the reaction tubes and test procedure are similar to those described in Example 3 except that either erythrocytes of a known antigenic composition (antibody screening) or donor erythrocytes (compatibility testing) are used in combination with a serum specimen from a patient or donor.

A. Results/Interpretation

If the patient's or donor's serum specimen contains an IgG antibody or antibodies directed against an antigen or antigens present on the erythrocytes used in the test procedure, the erythrocytes will adhere to the Protein G agarose particles at the top of the matrix (FIG. 1A).

In the case of a weak antigen-antibody reaction, some erythrocytes will adhere to the Protein G agarose particles at the top of the matrix and some will collect at the bottom of the reaction tube (FIG. 1B). If the serum specimen does not contain antibodies the antigens present on the erythrocytes, all the erythrocytes will collect at the bottom of the reaction tube (FIG. 1C). The results observed in this experiment are shown below in Table 4.

TABLE 4

| Antibody Specificity | No. of Examples Tested | No. Positive |
| --- | --- | --- |
| Anti-D | 1 | 1 |
| Anti-c | 1 | 1 |
| Anti-e | 1 | 1 |
| Anti-K | 4 | 4 |
| Anti-Fy$^a$ | 3 | 3 |
| Anti-Fy$^b$ | 2 | 2 |
| Anti-Jk$^a$ | 2 | 2 |
| Anti-Jk$^b$ | 2 | 2 |
| Anti-Xg$^a$ | 2 | 2 |

EXAMPLE 5

Testing for the Presence or Absence of the Rh D Antigen on Erythrocytes by Direct Assay Using an IgM Human Monoclonal Anti-D A. Preparation of Specific IgM Anti-D Agarose Beads Protein G will not directly bind IgM antibodies. Thus, in order to produce a gel capable of binding an IgM antibody, a bridging antibody may first be attached to the Protein G agarose beads. In the following example, a mouse monoclonal antibody specific for human kappa light chains was utilized to attach an IgM kappa light chain human monoclonal anti-D to the agarose beads.

Two ml of Immunopure® Immobilized Protein G were centrifuged for approximately two minutes at 1000 g and the supernate removed and discarded. Two ml of a pre-diluted sample of a mouse monoclonal anti-human kappa light chain (clone 5F3 mouse IgG1 isotype) were added. The monoclonal antibody containing culture supernate was diluted in 0.01M citrate buffered saline (pH 5.0). The contents were mixed gently and allowed to stand for 15 minutes. The agarose/antibody mixture was centrifuged for approximately two minutes at 1000 g and the supernate removed and tested for residual anti-kappa activity in an agglutination assay.

That testing was performed in the following manner: a sample of pre-diluted anti-kappa not incubated with the Protein G agarose beads and a sample of diluted anti-kappa that had been pre-incubated with the Protein G agarose beads were tested in parallel for their ability to agglutinate erythrocytes previously coated with an IgG kappa light chain antibody. The preincubated sample gave a negative reaction, indicating that all the anti-kappa had become attached to the Protein G agarose beads.

Two ml of a sample of a human monoclonal anti-D (clone GAMA-401 IgM kappa light chain) were added to the anti-kappa/Protein G agarose pellet. The monoclonal antibody containing culture supernate was diluted in 0.01M citrate buffered saline (pH 5.0). The contents were mixed gently and allowed to stand for 15 minutes. The agarose/antibody mixture was centrifuged for approximately two minutes at 1000 g and the supernate removed and tested for residual anti-D activity in an agglutination assay.

That testing was performed in the following manner: a sample of anti-D not incubated with the anti-kappa/Protein G agarose beads and a sample that had been pre-incubated with the anti-kappa/Protein G agarose beads were titrated in parallel and tested for their ability to agglutinate Rh D positive erythrocytes. The pre-incubated sample produced a significant reduction in titration value, indicating that anti-D had become attached to the matrix.

The anti-D/anti-kappa/Protein G agarose beads were washed three times with 0.85% NaCl in order to remove any unbound anti-D. After the final wash, two ml of a 0.01M citrate buffered saline solution (pH 5.0) containing 7.5% Dextran (w/v) were added to the beads and mixed thoroughly.

The erythrocytes were obtained from citrated blood samples which had been previously typed using FDA approved anti-D bloodgrouping reagents. A 0.8% suspension of erythrocytes was prepared in a low ionic strength solution (Gamma N-HANCE®, Gamma Biologicals, Inc.).

The preparation of the reaction tubes and test procedure are substantially identical to those previously described in Example 1.

A. Results/Interpretation

If the erythrocytes possess a normal expression of the Rh D antigen, they will adhere to the anti-D agarose particles at the top of the solid phase matrix (FIG. 1A). If the erythrocytes possess a weak (quantitative) expression of the D antigen, e.g., weak D, formerly called D", then some will adhere to the anti-D agarose particles at the top of the matrix and some will collect at the bottom of the reaction tube (FIG. 1B). If the erythrocytes do not possess the rhesus D antigen, all the erythrocytes will collect at the bottom of the reaction tube (FIG. 1C). The that were observed in this list are shown by low in Table 5.

TABLE 5

| | Rh D Positive | Rh D Negative | Weak D |
| --- | --- | --- | --- |
| No. Tested | 8 | 5 | 2 |
| No. Positive | 8 | 0 | 2 |

Testing erythrocytes for the presence or absence of other bloodgroup antigens with IgM antibodies can be performed in a similar manner.

Additional advantages and modifications will be readily apparent to those skilled in the art. The invention in its broader aspects is therefore not limited to the specific details or representative examples described. Accordingly, departures may be made from the detail without departing from the spirit or scope of the disclosed general inventive concept.

What is claimed is:

1. A method for detecting a bloodgroup antigen on erythrocytes, comprising the steps of:

obtaining a sample of erythrocytes to be tested;

adding said sample to a reaction tube, said tube having a lengthwise axis and containing two layers of immunoreactive particles; wherein said particles in the first layer of immunoreactive particles have Protein G ligand coupled to the surface of said particles and antibodies specific for said bloodgroup antigen coupled to said ligand on said particles and wherein said particles in the second layer of immunoreactive particles have immunoglobulin-binding ligand Protein A coupled to the surface of said particles, and a buffer solution, said first layer of immunoreactive particles positioned in the upper portion of said reaction tube and said second layer positioned below said first layer of immunoreactive particles;

centrifuging said reaction tube for a time sufficient to pellet to the bottom of said reaction tube erythrocytes that do not attach to said antibodies on said immunoreactive particles;

detecting attachment of said erythrocytes to said particles or lack thereof; and correlating attachment with the presence of said bloodgroup antigen.

2. A method for detecting a bloodgroup antigen on erythrocytes, comprising the steps of:

obtaining a sample of erythrocytes to be tested;

adding said sample to a reaction tube, said tube having a lengthwise axis and containing two layers of immunoreactive particles; wherein said particles in the first layer of immunoreactive particles have Protein G ligand, coupled to the surface of said particles, a bridging antibody coupled to said ligand and antibodies specific for said bloodgroup antigen coupled to said bridging antibody on said particles wherein the particles in the second layer of immunoreactive particles have immunoglobulin-binding ligand Protein A coupled to the surface of said particles, and a buffer solution, said first layer of immunoreactive particles positioned in the upper portion of said reaction tube and said second layer positioned below said first layer of immunoreactive particles;

centrifuging said reaction tube for a time sufficient to pellet to the bottom of said reaction tube erythrocytes that do not attach to said antibodies coupled to said bridging antibodies that are coupled to said ligands on said immunoreactive particles;

detecting attachment of said erythrocytes to said particles or lack thereof, and correlating attachment with the presence of said bloodgroup antigen.

3. A method for detecting a blood cell antigen in blood typing, comprising the steps of:

obtaining a sample of erythrocytes to be tested;

incubating said erythrocytes in a reaction tube with a preparation of antibodies specific for a known blood cell antigen under conditions and for a time sufficient to bind said antibodies to said antigens if said antigens are present, said tube having a lengthwise axis and also containing two layers of immunoreactive particles; wherein said particles in the first layer of immunoreactive particles have Protein G ligand, coupled to the surface of said particles and wherein the particles in the second layer of immunoreactive particles have immunoglobulin-binding ligand Protein A coupled to the surface of said particles, and a buffer solution, said first layer of immunoreactive particles positioned in the upper portion of said reaction tube and said second layer positioned below said first layer of immunoreactive particles;

centrifuging said reaction tube for a time sufficient to pellet to the bottom of said reaction tube erythrocytes that do not attach to said ligand on said immunoreactive particles; and correlating attachment of said erythrocytes to said particles with the presence of said antigen on said erythrocytes.

4. A method for detecting blood serum or plasma antibodies specific for blood cell antigens, comprising the steps of:

obtaining a sample of erythrocytes having known antigens on the surface thereof;

obtaining a sample of a blood component selected from the group consisting of serum and plasma to be tested for antibodies against said antigen;

incubating said erythrocytes and said blood component sample in a reaction tube under conditions and for a time sufficient for said antibodies to bind to said antigens on said erythrocytes if said antibodies are present, said tube having a lengthwise axis and also containing two layers of immunoreactive particles; wherein said particles in the first layer of immunoreactive particles have Protein G ligand, coupled to the surface of said particles and wherein the particles in the second layer of immunoreactive particles have immunoglobulin-binding ligand Protein A coupled to the surface of said particles, and a buffer solution, said first layer of immunoreactive particles positioned in the upper portion of said reaction tube and said second layer positioned below said first layer of immunoreactive particles;

centrifuging said reaction tube for a time sufficient to pellet to the bottom of said reaction tube erythrocytes that do not attach to said ligand on said immunoreactive particles; and correlating attachment of said erythrocytes to said particles with the presence of said antibodies.

5. The method of claims 1 or 3, wherein said antibodies are selected from the group consisting of anti-A, anti-B, anti-AB, anti-D, anti-C, anti-c, anti-E, anti-e, anti-K, anti-Fy$^a$, anti-Fy$^b$, anti-Jk$^a$, anti-Jk$^b$, anti-S and anti-s.

6. The method of claims 1, 2, 3 or 4, wherein said centrifuging is performed using a centrifuge having a rotor adapted so that a centrifugal force generated by said centrifuging acts along the axis of said reaction tube.

7. The method of claim 6, wherein said centrifuging is performed for a time ranging from about 10–30 seconds in a range from about 800–1200 g, for a time ranging from about 15–45 seconds in a range from about 300–600 g, and for a time ranging from about 45–90 seconds in a range from about 1300–1600 g.

8. The method of claim 1, wherein said second layer of immunoreactive particles have antibodies specific for said bloodgroup antigen coupled to said ligand on said particles.

9. The method of claims 1, 2, 3, or 4, wherein said first layer of immunoreactive particles are of a material selected from the group consisting of agarose, Sepharose and latex.

10. The method of claims 1, 2, 3, or 4, wherein said second layer of immunoreactive particles are of a plastic material.

11. The method of claims 1, 2, 3, or 4, wherein said second layer of immunoreactive particles are selected from the group consisting of Sephacryl S-100, Sephacryl S-200, and Sephacryl S-400.

12. The method of claims 1, 2, 3, or 4, wherein said erythrocytes are prepared for testing in a low ionic strength solution creating an about 0.5–1.0% (w/v) suspension of said erythrocytes.

13. The method of claim 4, wherein said known antigens are selected from a group consisting of A, B, D, C, c, $C^w$, E, e, K, $FY^a$, $Fy^b$, $Jk^a$, $Jk^b$, S and s.

14. The method of claim 4, wherein said antibody tested for is selected from the group consisting of anti-A, anti-B, anti-AB, anti-D, anti-C, anti-c, anti-E, anti-e, anti-K, anti-$Fy^a$, anti-$Fy^b$, anti-$Jk^a$, anti-$Jk^b$, anti-S and anti-s.

15. The method of claim 3, wherein the antigen tested for is selected from the group consisting of A, B, D, C, c, $C^w$, E, e, K, $Fy^a$, $Fy^b$, $JK^a$, $Jk^b$, S and s.

* * * * *